US00PP33525P2

(12) United States Plant Patent
Van Swieten

(10) Patent No.: US PP33,525 P2
(45) Date of Patent: Sep. 28, 2021

(54) ***PHALAENOPSIS* ORCHID PLANT NAMED 'PHA1493891'**

(50) Latin Name: ***Phalaenopsis* hybrid**
Varietal Denomination: PHA1493891

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,217

(22) Filed: Apr. 15, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHA1493891', particularly characterized by white, shaded, and striped flowers with red and white striped lips, flowers with a flat shape in lateral view, apical lobes with a small bump and ridge, and is propagated by meristem tissue culture, is disclosed.

3 Drawing Sheets

Genus and species: *Phalaenopsis* hybrid.
Variety denomination: 'PHA1493891'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA1493891'.

The new *Phalaenopsis* plant is a product of a planned breeding program conducted by the inventor in Bleiswijk, the Netherlands. The objective of this breeding program was to create a new *Phalaenopsis* plant with white, shaded, and striped flowers with red and white striped lips, suitable for potted plant production.

The new *Phalaenopsis* plant 'PHA1493891' is a result of cross-pollination made by the inventor in April 2010 in Bleiswijk, the Netherlands, of the proprietary female, or seed parent, *Phalaenopsis* hybrid 'PHALFOYX' (U.S. Plant Pat. No. 28,103) with the proprietary male, or pollen parent, *Phalaenopsis* hybrid '22444-010' (unpatented).

The new *Phalaenopsis* was selected by the inventor as a single plant within the progeny of the stated cross-pollination in a controlled greenhouse in Bleiswijk, the Netherlands, in March 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 22, 2020 (Application no. 2020/2306), by Applicant who obtained the subject matter disclosed directly from the inventor. 'PHA1493891' has not been made publicly available or sold anywhere in the world prior to the effective filing date of this application with the exception of sales or disclosures made one year or less before the effective filing date of this claimed invention by Applicant who obtained 'PHA1493891' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA1493891' as a new and distinct variety of *Phalaenopsis* plant:

1) White, shaded, and striped flowers with red and white striped lips;
2) Flower shape in lateral view is flat; and
3) Apical lobe has a small bump and ridge.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in February 2021. Colors in the photographs may differ from the color values cited in the detailed botanical description, which accurately describe the actual colors of the new variety.

DESCRIPTION OF THE NEW VARIETY

Figure 1:
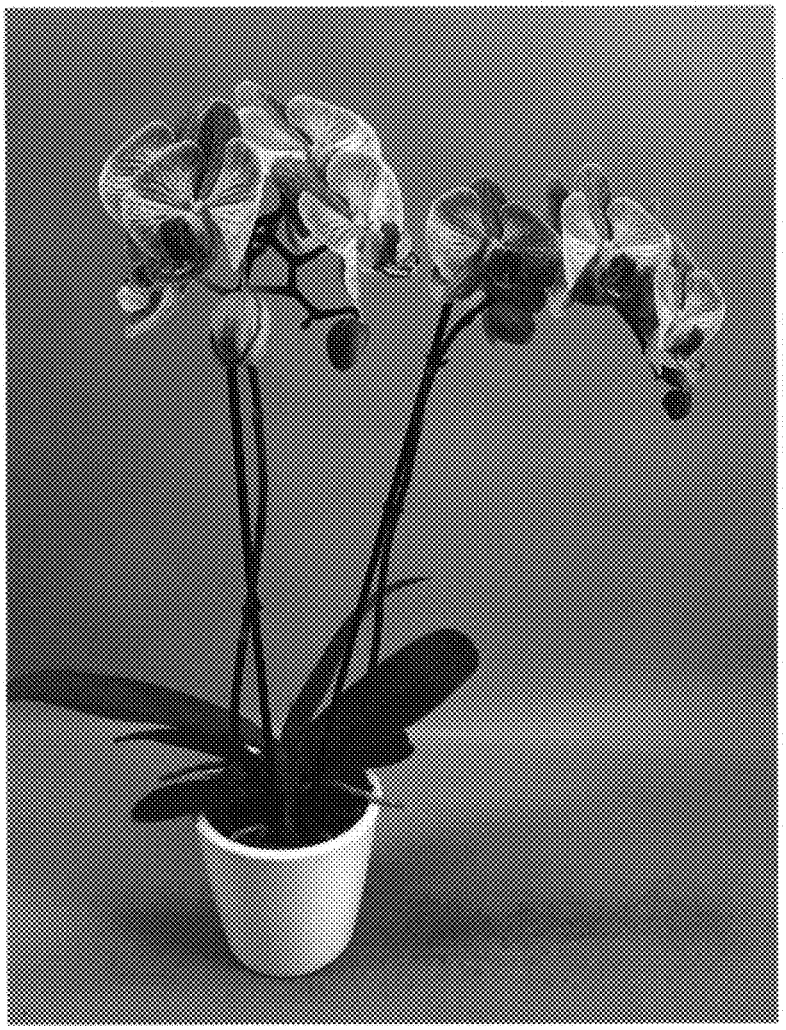
FIG. 1 shows the overall plant habit, including blooms, buds, and foliage of 'PHA1493891'.
Figure 2:
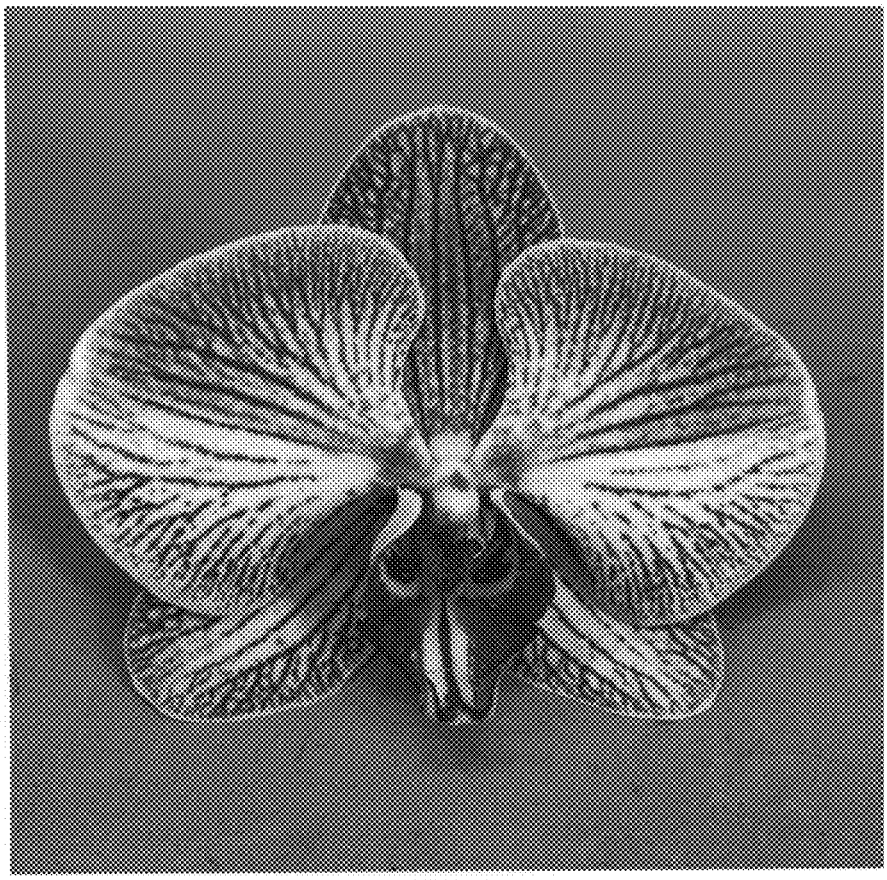
FIG. 2 shows a close-up of a flower of 'PHA1493891'.
Figure 3:
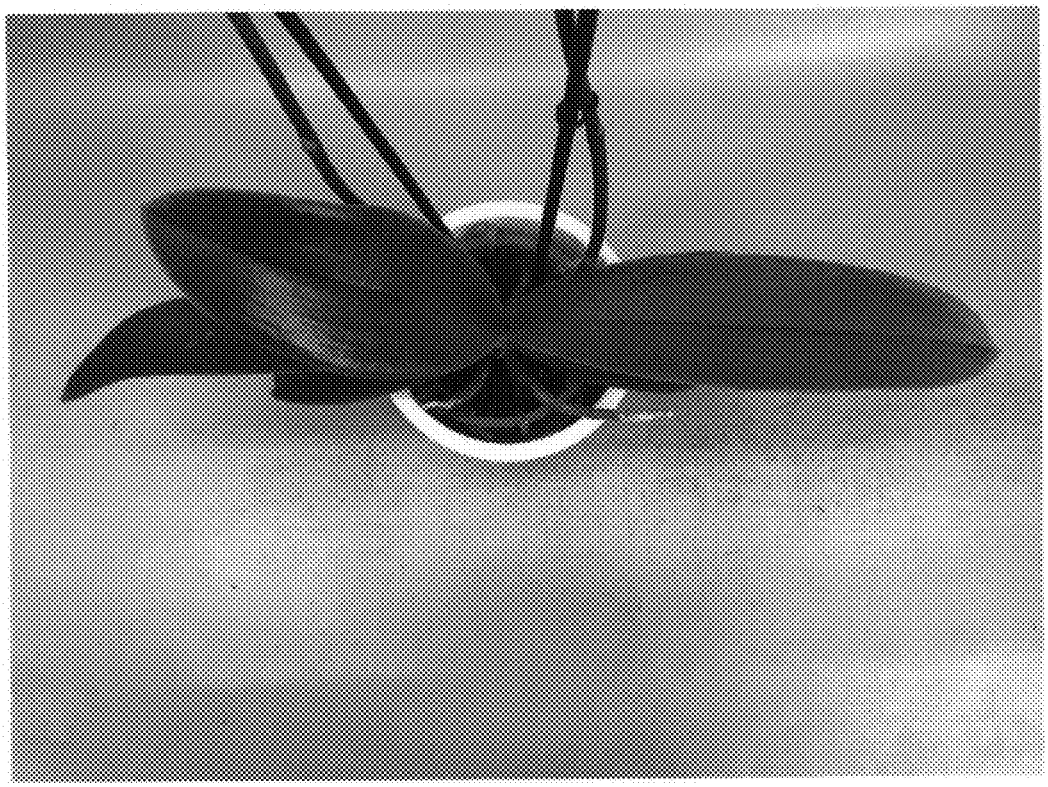
FIG. 3 shows an overhead view of the leaves of 'PHA1493891'.

The following detailed description sets forth the distinctive characteristics of 'PHA1493891'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA1493891'.

Parentage:

*Female parent*.—*Phalaenopsis* cultivar 'PHALFOYX' (U.S. Plant Pat. No. 28,103).

*Male parent*.—*Phalaenopsis* cultivar '22444-010' (unpatented).

Propagation:

*Type*.—Meristem tissue culture.

Roots:

*Root description*.—Greyed-green (a color in between RHS 190B and RHS 190C) colored roots with branching lateral roots having yellow-green (a color in between RHS N144A and RHS 145C) with a hint of purplish-red (a color in between RHS N77B and RHS N79C) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 52.0 cm to 57.0 cm.

*Width* (*measured from leaf tips*).—About 39.0 cm to 41.0 cm.

*Vigor*.—Strong.

Leaves:

*Mature leaves*.—Quantity per plant: 6 to 7 leaves are produced before flowering. Length (fully expanded): 21.0 cm to 23.0 cm. Width: 6.5 cm to 7.5 cm. Position of the broadest part of the leaf: At the middle. Shape: Oblong. Base shape: Moderately elongated. Apex: Obtuse unequal. Leaf blade angle with the petiole (measured from the horizontal position): Between 10 degrees and 30 degrees. Leaf margin: Entire. Color: Upper surface: RHS 146B. Lower surface: RHS 146C. Texture (both upper and lower surfaces): Smooth. Thickness: 2.0 mm to 3.0 mm. Variegation: Absent. Venation: Pattern: Parallel. Color of the midvein: Upper surface: RHS 146B. Lower surface: RHS 144A.

Peduncle:

*Quantity per plant*.—1 to 2.

*Number of flowers per peduncle*.—7 to 9.

*Length*.—52.0 cm to 57.0 cm.

*Diameter*.—5.0 mm to 6.0 mm.

*Strength*.—Strong.

*Aspect*.—Upright to slightly pendent.

*Texture*.—Smooth.

*Color*.—Green (RHS 146C) with a touch of dark brown (a color in between RHS 187B and RHS 200C).

*Internode length*.—4.0 cm to 5.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 140.0 mm to 170.0 mm.

*Flowering time*.—First flowers can be expected 10 to 11 months after planting in a 12-cm pot.

*Flower*.—Height: 85.0 mm to 90.0 mm. Diameter: 95.0 mm to 100.0 mm. Depth of lip: 24 0 mm to 26.0 mm.

*Flower longevity*.—On the plant: 24 to 26 weeks.

*Flower shape*.—Flat.

*Fragrance*.—Absent.

*Flower bud*.—Average size: Large. Length: 28.0 mm to 30.0 mm. Width: 23.0 mm to 25.0 mm. Shape: Egg shaped. Color: Yellow-green (RHS N144D) at the base; light yellow-green (RHS 145C); purplish-red (RHS N77B) toward the tip with diluting dark purplish-red stripes (RHS N79C).

*Petals*.—Arrangement: Open/free. Shape: Semi-circular. Apex: Emarginated asymmetric. Margin: Weakly undulated. Length (from base to tip): 45.0 mm to 47.0 mm. Width: 55.0 mm to 57.0 mm. Position of the broadest part of the petal: Toward the base. Color (when fully opened): Upper surface: Basic color: White (RHS NN155D). Over color: Purplish-pink (RHS N78C) at the base; reddish-purple stripes (RHS N78A) and shade (RHS N78C). Lower surface: Basic color: White (RHS NN155D). Over color: Light reddish-purple shade (RHS N78D) at the base, which becomes lighter toward margin on one side (from RHS 76A to RHS 76B); diluting stripes (RHS N78C). Number of spots and stripes on the petals (upper surface): Many stripes. Color of spots and stripes on the petals (upper surface): RHS N78A. Density of netting of the petals (upper surface): None. Color of the netting (upper surface): Not applicable.

*Dorsal sepal*.—Shape: Elliptic. Apex: Obtuse symmetric. Margin: Moderately undulated. Length (from base to tip): 49.0 mm to 51.0 mm. Width: 31.0 mm to 33.0 mm. Position of the broadest part of the dorsal sepals: At the middle. Color (when fully opened): Upper surface: Basic color: Reddish-purple (RHS N78B). Over color: Touch of white (RHS NN155D) at the base; reddish-purple stripes and netting (RHS N78A). Lower surface: Basic color: Light purple (RHS 76A). Over color: Light reddish-purple (RHS N78D); diluting stripes (RHS N78C). Number of spots and stripes on the dorsal sepals (upper surface): Medium stripes. Color of spots and stripes on the dorsal sepals (upper surface): RHS N78A. Density of netting of the dorsal sepals (upper surface): Medium. Color of the netting: RHS N78A.

*Lateral sepals*.—Shape: Ovate. Apex: Obtuse symmetric. Margin: Moderately undulated. Length (from base to tip): 50.0 mm to 52.0 mm. Width: 30.0 mm to 32.0 mm. Position of the broadest part of the lateral sepals: At the base. Color (when fully opened): Upper surface: Basic color: White (RHS NN155D). Over color: Light yellow-green (RHS 145D) with few purplish-red flecks (RHS 71A) at the base; reddish-purple stripes and netting (RHS N78B); light reddish-purple shade (RHS N78D) toward the tip. Lower surface: Basic color: Very light purple (RHS 76B). Over color: Light reddish-purple shade (RHS N78D) and yellow-green (RHS 145C) at the base; purplish-pink midvein (RHS N78C); diluting stripes (RHS N78B). Number of spots, flecks, and stripes on the lateral sepals (upper surface): Few flecks at the base and medium stripes. Color of spots, flecks, and stripes on the lateral sepals (upper surface): Flecks (RHS 71A) and stripes (RHS N78B). Density of netting of the lateral sepals (upper surface): Low. Color of the netting (upper surface): RHS N78B.

*Labellum* (*lip*).—Whiskers: Present. Length of whiskers: 21.0 mm to 23.0 mm. Color of whiskers: Dark red (RHS 59A) toward margin on one side and white (RHS NN155C) toward margin on the other side; reddish-purple (RHS N78A) at the middle and light greenish-yellow tips (RHS 4B). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Moderately undulated. Length: 21.0 mm to 23.0 mm. Width: 15.0 mm to 17.0 mm. Color: Upper surface: White (RHS NN155C); hint of greenish-yellow (RHS 6A) with few stripes (a color in between RHS 59A and RHS 59B) at the base; red (RHS 180A) toward margin on one side; reddish-purple stripes (RHS N78B) toward the tip. Lower surface: White (RHS NN155C); greenish-yellow (RHS 6A) flecked (RHS 184A) on one side toward the margin; very light purple (a color in between RHS 76B and RHS 76C) on one side toward the tip. Number of spots and stripes on the lateral lobe: Medium to many stripes. Color of spots and stripes on the lateral lobe: Few stripes at the base (a color in between RHS 59A and RHS 59B) and toward the tip (RHS N78B). Density of netting of the lateral lobe: None. Color of the netting: Not applicable.

*Apical lobe*.—Shape: Triangular. Margin: Entire. Length: 21.0 mm to 23.0 mm. Width: 24.0 mm to 26.0 mm. Color: Upper surface: Touch of greenish-yellow (RHS 6C) at the base and tip; red midvein and wings (RHS 60A); white (RHS NN155D); reddish-purple stripes (RHS N78A) toward margins and whiskers. Lower surface: Very light purple (RHS 76B) at the middle from base toward whiskers; light greenish-yellow (RHS 160C) toward wings; dark red margins (a color in between RHS 59A and RHS 59B); white (RHS NN155C) toward whiskers. Number of spots and stripes on the apical lobe: Few to medium stripes. Color of spots and stripes on the apical lobe: RHS N78A. Density of netting of the apical lobe: None. Color of the netting: Not applicable. Bump and ridge: Present (small).

*Callus*.—Average size: Large. Height: 8.0 mm to 9.0 mm. Length: 8.0 mm to 9.0 mm. Width: 4.0 mm to 5.0 mm. Color: Yellow (RHS 12A): white (RHS NN155C) on sides; dotted (RHS 183C).

Reproductive organs:

*Column*.—Length: 9.0 mm to 11.0 mm. Diameter: 5.0 mm to 6.0 mm. Color: White (RHS NN155C) with light purple ring (RHS 76A) at the middle and few reddish-purple stripes (RHS N78B).

*Pollinia*.—Quantity: 2. Diameter: 0.9 mm to 1.1 mm. Color: Orange (RHS 25A).

*Ovary*.—Length: 12.0 mm to 14.0 mm. Diameter: 2.4 mm to 2.6 mm.

*Pedicel*.—Length: 34.0 mm to 36.0 mm. Diameter: 2.7 mm to 3.0 mm. Color: Yellow-green (RHS 195B) with a touch of purplish-red (RHS N77B); light reddish-purple (RHS N78D) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA1493891' differs from the female parent plant 'PHALFOYX' (U.S. Plant Pat. No. 28,103) in that 'PHA1493891' has obtuse dorsal sepal apexes and striped apical lobes, whereas 'PHALFOYX' has emarginated dorsal sepal apexes and dotted apical lobes.

'PHA1493891' differs from the male parent plant '22444-010' (unpatented) in that 'PHA1493891' has flowers with a striped and shaded pattern and whiskers that are dark red toward margin on one side and white toward margin on the other side with reddish-purple at the middle and light greenish-yellow tips, whereas '22444-010' has flowers with an even pattern and whiskers that are greenish-yellow.

'PHA1493891' is most similar to the commercial *Phalaenopsis* plants named 'PHALCTOZYP' (U.S. Plant Pat. No. 27,670) and 'PHALDOQAH' (U.S. Plant Pat. No. 27,457). 'PHA1493891' differs from the commercial variety 'PHALCTOZYP' in that 'PHA1493891' has large calluses, dorsal sepals with a basic color of reddish-purple, and flowers with a striped and shaded pattern, whereas 'PHALCTOZYP' has medium calluses, dorsal sepals with a basic color of white, and flowers with a striped and dotted pattern.

'PHA1493891' differs from the commercial variety 'PHALDOQAH' in that 'PHA1493891' has dorsal sepals with a basic color of reddish-purple, flowers with a striped and shaded pattern, and petals with a basic color of white, whereas 'PHALDOQAH' has dorsal sepals with a basic color of white, flowers with a striped and netted pattern, and petals with a basic color of light purple.

I claim:

1. A new and distinct variety of *Phalaenopsis* plant named 'PHA1493891', substantially as described and illustrated herein.

* * * * *